(12) United States Patent
Kinoshita et al.

(10) Patent No.: US 8,579,803 B2
(45) Date of Patent: Nov. 12, 2013

(54) ENDOSCOPE

(75) Inventors: Hiroaki Kinoshita, Akishima (JP); Atsushi Goto, Tachikawa (JP); Daisuke Akiyama, Fuchu (JP); Takeshi Suga, Hino (JP); Shinji Egami, Akishima (JP); Makoto Tanabe, Hachioji (JP); Akihito Miyata, Akiruno (JP); Takuya Takechi, Hachioji (JP); Masao Akai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 28 days.

(21) Appl. No.: 13/445,388

(22) Filed: Apr. 12, 2012

(65) Prior Publication Data

US 2012/0289779 A1  Nov. 15, 2012

Related U.S. Application Data (63) Continuation of application No. PCT/JP2011/073402, filed on Oct. 12, 2011.

(30) Foreign Application Priority Data

Oct. 12, 2010  (JP) .................................. 2010-229986

(51) Int. Cl.
*A61B 1/04* (2006.01)

(52) U.S. Cl.
USPC ........................................... 600/182; 501/37

(58) Field of Classification Search
USPC ........ 428/98; 600/182; 501/37; 385/123, 142
See application file for complete search history.

(56) References Cited

U.S. PATENT DOCUMENTS

2004/0220038 A1  11/2004  Wolff et al.

FOREIGN PATENT DOCUMENTS

| EP | 1 452 495 | 9/2004 |
|---|---|---|
| JP | 58-077304 | 5/1983 |
| JP | 59-128501 | 7/1984 |
| JP | 06-003536 | 1/1994 |
| JP | 2004-256389 | 9/2004 |
| JP | 2004-277281 | 10/2004 |
| JP | 2009-007194 | 1/2009 |
| JP | 2011-116621 | 6/2011 |

OTHER PUBLICATIONS

International Search Report, issued in corresponding International Patent Application No. PCT/JP2011/073402.

*Primary Examiner* — Alexander Thomas
(74) *Attorney, Agent, or Firm* — Kenyon & Kenyon LLP

(57) ABSTRACT

An endoscope includes an insertion portion including an image pickup section, an illumination section, and a light guide inserted inside the insertion portion, the light guide including a plurality of fibers made of a glass not containing lead, the plurality of fibers guiding illuminating light from a light source apparatus to the illumination section, the light guide having a numerical aperture of 0.46 to 0.90. A core glass of a fiber have a refractive index nd of 1.56 to 1.74, and a composition of (A) 20 to 55 wt % $SiO_2$, (B1) 0 to 4.0 wt % $B_2O_3$, (B2) neither $P_2O_5$ nor $GeO_2$ contained, (C) 25 to 72 wt % ($BaO+SrO+La_2O_3+Lu_2O_3+Ta_2O_5+Gd_2O_3+WO_3$), (D) 0 to 30 wt % ZnO, (E) no $Al_2O_3$ contained, (F) no $ZrO_2$ contained, (G) neither PbO nor $As_2O_3$ contained, (H) 0 to 15 wt % ($Na_2O+K_2O$), (I) 0 to 0.050 wt % $Sb_2O_3$ and (J) 0.26 to 1.63 wt % ($Na_2SO_4+K_2SO_4$).

14 Claims, 8 Drawing Sheets

őŐ# ENDOSCOPE

CROSS REFERENCE TO RELATED APPLICATION

This application is a continuation application of PCT/JP2011/073402 filed on Oct. 12, 2011 and claims benefit of Japanese Application No. 2010-229986 filed in Japan on Oct. 12, 2010, the entire contents of which are incorporated herein by this reference.

BACKGROUND OF THE INVENTION

1. Field of the Invention

Embodiments of the present invention relate to endoscopes including a light guide, and specifically relate to endoscopes including a light guide made of lead-free glass.

2. Description of the Related Art

Medical endoscopes need to illuminate an object to observe an inside of a dark body cavity. Thus, a light guide (LG) is used for guiding light generated by a light source apparatus to an illumination section disposed in a distal end portion of an insertion portion of the endoscope.

Figure 1:
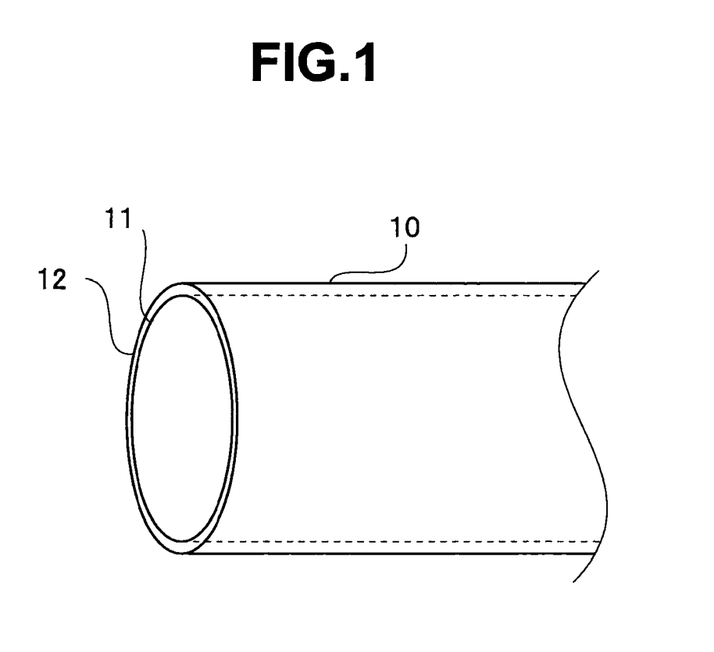
FIG. 1 is a diagram illustrating a structure of a light guide fiber.

A light guide has a configuration in which numerous optical fibers are bundled. As illustrated in FIG. 1, an individual fiber 10 includes a core 11 that transmits light, and a clad 12 provided on an outer circumferential portion of the core 11, the clad 12 reflecting light so as to prevent the light from leaking from a side face of the core to the outside. A high-refractive index glass is used for the core 11 and a glass having a refractive index lower than that of the core 11 is used for the clad 12.

For core glass for normal LGs, glass containing lead, i.e., what is called lead glass, is used. This is because lead glass has the advantages of, e.g., low price, easy fiber manufacturing and good transmittance. In recent years, in order to respond to environmental problems, glass with no lead used therein (hereinafter also referred to as "lead-free glass") has been developed. For example, Japanese Patent Application Laid-Open Publication Nos. 2004-256389 and 2004-277281 each disclose lead-free aluminosilicate glass.

Here, with medical endoscopes, not only normal-light imaging using white color light, but also various types of special light imaging using wavelength characteristics of illuminating light are performed. For example, narrow band imaging (NBI) is a method in which hemoglobin in blood is irradiated with light having two narrowed wavelength bands that are easily absorbed in blood, for example, illuminating light in a first wavelength band of 390 to 445 nm and light in a second wavelength band of 530 to 550 nm to highlight capillary vessels in a superficial layer of a mucous membrane and a fine pattern of the mucous membrane, thereby easily discriminating a tumor tissue. In the method, image information in a blue color light range is very important.

Also, in some of the models of the medical endoscopes, for example, endoscopes for small intestine, large intestine, a pancreatobiliary region or renal pelvis and ureter, an X-ray may be applied to confirm a position of the endoscope inserted in a body.

Also, Japanese Patent Application Laid-Open Publication No. 2009-7194 discloses lead-free glass containing a rare-earth oxide and having radiation blocking ability. Furthermore, for communication fibers used under strong radiation exposure environments such as nuclear power plants, quartz-based optical fibers that contain a CH group or an OH group for enhancement of the radiation resistant characteristic are used. Furthermore, Japanese Patent Application Laid-Open Publication No. 59-128501 discloses an outer circumferential portion of a broadband optical fiber containing quartz as its main material, which is used under a high radiation environment containing neutrons, being covered by metal coating.

Furthermore, Japanese Patent Application Laid-Open Publication No. 2011-116621 discloses glass for a light guide for an endoscope.

SUMMARY OF THE INVENTION

An endoscope according to an aspect of the present invention includes: an insertion portion including an image pickup section and an illumination section in a distal end portion thereof; and a light guide inserted through an inside of the insertion portion, the light guide including a plurality of fibers made of a glass not containing lead, the plurality of fibers guiding illuminating light from a light source apparatus connected to a proximal end portion side to the illumination section, the light guide having a numerical aperture (NA) of 0.46 to 0.90, wherein a core glass of the fiber have a refractive index nd of 1.56 to 1.74, and has a composition of (A) 20 to 55 wt % $SiO_2$, (B1) 0 to 4.0 wt % $B_2O_3$, (B2) neither $P_2O_5$ nor $GeO_2$ contained, (C) 25 to 72 wt % ($BaO+SrO+La_2O_3+Lu_2O_3+Ta_2O_5+Gd_2O_3+WO_3$), (D) 0 to 30 wt % ZnO, (E) no $Al_2O_3$ contained, (F) no $ZrO_2$ contained, (G) neither PbO nor $As_2O_3$ contained, (H) 0 to 15 wt % ($Na_2O+K_2O$), (I) 0 to 0.050 wt % $Sb_2O_3$ and (J) 0.26 to 1.63 wt % ($Na_2SO_4+K_2SO_4$).

DETAILED DESCRIPTION OF THE PREFERRED EMBODIMENTS

First Embodiment

Figure 2:
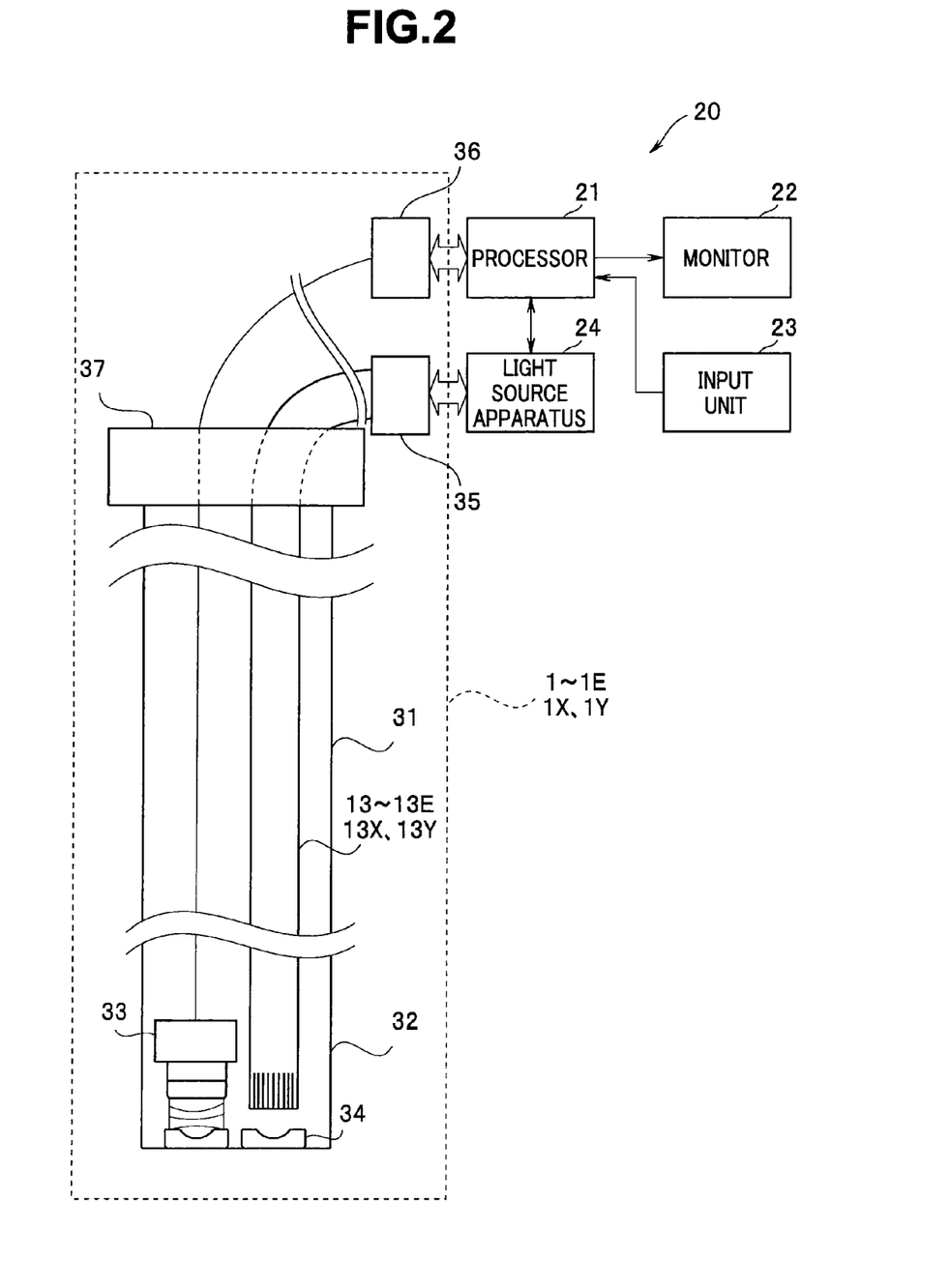
FIG. 2 is a diagram of a configuration of an endoscope system including an endoscope according to a first embodiment.

As illustrated in FIG. 2, a medical endoscope system 20 including an endoscope 1 according to a first embodiment includes a processor 21 that processes an image signal, a monitor 22 that displays an endoscopic image, an input unit 23 for a user to set, e.g., use conditions, and a light source apparatus 24.

The endoscope 1 is an electronic endoscope including: an insertion portion 31 including an image pickup section 33 that picks up a color endoscopic image and an illumination section 34 at a distal end portion 32; a light guide 13 inserted through an inside of the insertion portion 31, the light guide 13 guiding illuminating light from the light source apparatus 24 connected to the endoscope via a light guide connector 35 on the proximal end portion side to the illumination section 34; and an electronic connector 36 connecting the image pickup section 33 that includes, e.g., a CCD, and the processor 21.

Here, the endoscope 1 enables special-light imaging (NBI) using illuminating light in a first wavelength band of 390 to 445 nm and illuminating light in a second wavelength band of 530 to 550 nm.

For example, the insertion portion 31 includes a flex, a corrugated tube and the like made of SUS304 and having a thickness of 0.2 mm at an outer circumferential portion in order to maintain moderate bendability, in addition to the LG 13, and has an outer diameter of 15 mm. For lower invasiveness, reduction in diameter of the insertion portion 31 is important, and therefore, as described later, a diameter of the light guide 13 is reduced to, for example, 1.8 mm.

<Fiber Manufacturing Method>

Here, a method for manufacturing a light guide fiber will briefly be described. As already described, a light guide fiber 10 includes a clad 12 made of a low-refractive index glass on an outer circumferential portion of a core 11 made of a high-refractive index glass that transmits light, the clad 12 reflecting light so as to prevent the light from leaking from a side face of the core.

Examples of the method for manufacturing the light guide fiber 10 include a preform method. In the preform method, first, a preform having a large clad diameter and a large core diameter is manufactured using, e.g., a rod-in-tube method or a double crucible method. In the rod-in-tube method, a rod made of core glass is inserted into a hollow portion of a tube made of clad glass, and then heated from an outer circumferential portion of the glass by, e.g., an electric furnace to provide flexibility, and then, subjected to spinning, that is, heating and stretching to obtain a fiber 10 having a desired diameter. In the double crucible method, a double crucible, that is, a crucible that melts core glass and a crucible surrounding that crucible and melting clad glass, are installed, a nozzle that extrudes molten clad glass is disposed around a nozzle that extrudes molten core glass, and the molten core glass and the molten clad glass are simultaneously drawn out from the respective nozzles and spun, thereby obtaining a fiber having a desired diameter fiber 10.

Clad glass has requirements such as (1) a refractive index nd that is smaller than that of core glass, (2) good chemical resistance, (3) a thermal expansion coefficient ($\alpha$) close to that of core glass, (4) crystallization does not occur in the glass at the time of fiber drawing, and (5) good adhesiveness to core glass.

Thus, for a clad glass material, which is selected from known lead-free glasses in consideration of compatibility with the core glasses according to the later-described embodiment, for example, a glass having a composition containing 41 to 46 wt % $SiO_2$, less than 14 wt % $B_2O_3$, less than 10 wt % $Al_2O_3$, less than 11 wt % $Na_2O$, less than 14 wt % $K_2O$, less than 1.5 wt % $Li_2O$ and less than 0.2 wt % F, and a customary amount of clarificant can be used.

Medical endoscopes need to illuminate an object in order to observe an inside of a dark body cavity. Thus, a light guide that guides light generated by a light source apparatus to an illumination section disposed in a distal end portion of an insertion portion of the endoscope is used. Light guides used for medical endoscopes require an NA of around 0.55 to 0.90, which is large compared to, e.g., communication fibers, because the light guide need to widely illuminate an inside of a body. For example, core glass needs to have a refractive index nd of 1.56 to 1.74, and for a material for clad glass, a material having a refractive index that is smaller than that, for example, a glass having a refractive index nd of 1.47 to 1.52 is selected.

Here, where a conventional lead-free glass LG is used for an endoscope that is subjected to X-ray irradiation, the lead-free glass LG has poor X-ray resistance and the core glass is colored, resulting in a decrease in light amount. In addition, the conventional lead-free glass LG does not recover much from the colored state. Thus, it can be considered as a first problem that where a doctor uses an endoscope including a conventional lead-free glass LG, the doctor has difficulty in conducting proper observation, examination and treatment.

In other words, as will be described later, for example, in a simulated test for an endoscope using an Xe light source, in which a conventional lead-free glass LG is mounted, where the light amount before X-ray irradiation is 100%, the light amount after X-ray irradiation/recovery processing is 30 to 60%, and under conditions in a stronger X-ray irradiation test, the light amount exhibits a percentage equal to or lower than such percentages. Furthermore, there is a large decrease specially in a blue range, and thus, the spectrum of the illuminating light largely changes and the RGB balance breaks down substantially, resulting in poor color rendition. The inventors presumed that the light amount decrease and color rendition deterioration due to X-ray irradiation are of levels in which where a doctor uses the endoscope, the doctor has difficulty in conducting proper observation, examination and treatment, and the inventors considered the light amount decrease and color rendition deterioration as a problem to be solved.

Next, in spectral imaging (special-light imaging), the light amount is decreased because a wavelength range of illuminating light is narrowed, and thus, it is necessary that brighter illuminating light be made to enter the LG. However, the inventors presumed that a conventional lead-free glass LG is subjected to coloring in a blue color range due to X-ray irradiation more than that in green and red ranges, resulting in increase in noise of an endoscopic image and such noise increase is of a level that there is difficulty in conducting proper spectral observation, examination and treatment, and the inventors considered such noise increase as a second problem.

A lead-contained glass LG also exhibits a light amount decrease due to X-ray irradiation. However, a lead-contained glass LG relatively quickly recovers from a colored state when white color light from the light source passes through the inside thereof, and thus, the problem that when a doctor uses the endoscope, an obtained endoscopic image is too dark for a doctor to perform, e.g., observation using the endoscope has not emerged.

Here, a number of fibers in an LG may be increased as a countermeasure for the light amount decrease. However, reduction in diameter of endoscopes is necessary for decreasing patients' discomfort, and thus, it is necessary to enhance the X-ray resistance while a predetermined outer diameter is maintained.

<Measurement Method>

Next, methods for light amount measurement and an X-ray resistance test will be described. For measurement, both an LG single body, which is a fiber bundle, and an endoscope with a LG mounted therein were used. First, measurement of the LG single body will be described.

Figure 3:
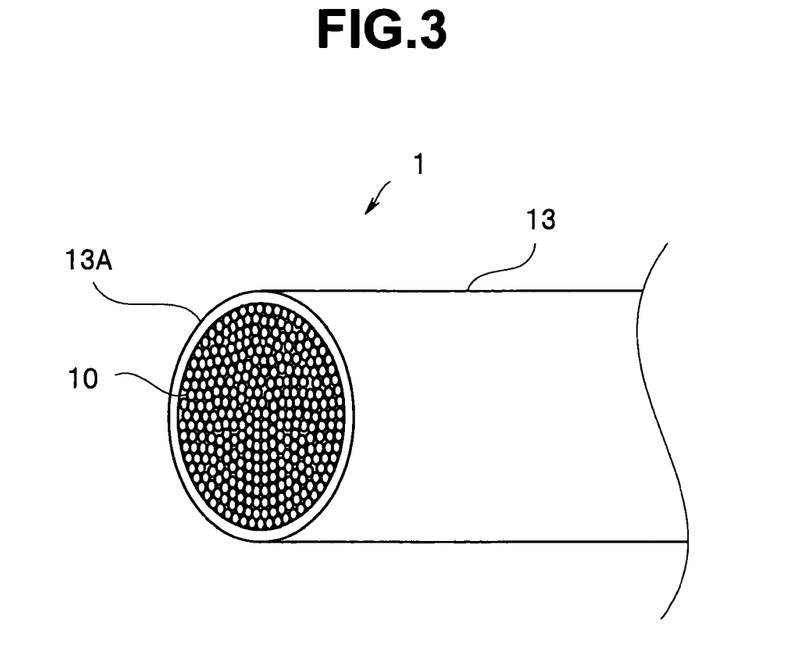
FIG. 3 is a diagram illustrating a structure of a fiber bundle.

For measurement of the LG single body, a fiber bundle (LG 13) having a diameter of 1.8 mm and a length of 1 m, which is illustrated in FIG. 3, manufactured by applying a silicone oil to surfaces of 2800 fibers each having a diameter of 30.0 μm and charging the fibers in a silicone tube having a thickness of 0.1 mm.

Figure 4:
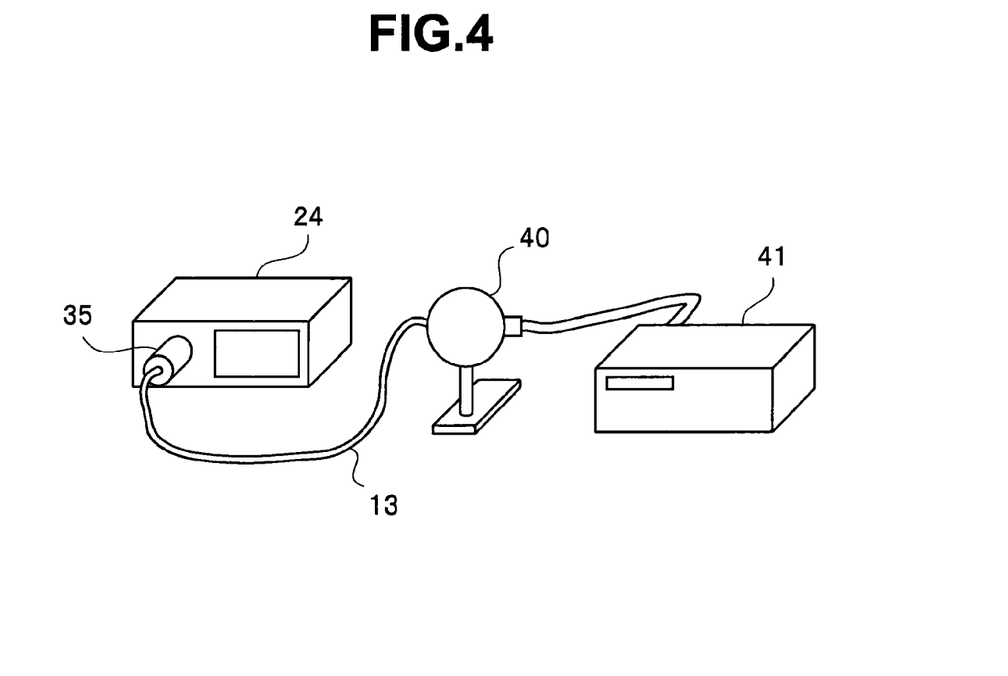
FIG. 4 is a diagram illustrating a light amount measurement method for a light guide for the endoscope according to the first embodiment.

As illustrated in FIG. 4, in light amount measurement, one end portion of the LG 13 is connected to the light source apparatus 24, and another end portion thereof is inserted into an integrating sphere 40. The integrating sphere 40 that includes an inner wall having a high optical reflectance and a high diffuseness uniformizes illuminating light from the LG 13 and guides the illuminating light to an actinometer 41. The light source apparatus 24 uses a xenon lamp as a light source, and generates light in an amount of 64 lumen/mm$^2$. In other words, the light guided into the LG 13 is measured in the actinometer 41 via the integrating sphere 40 having a sensibility that is the same as a spectral luminous efficiency of the xenon lamp light source in such a manner that an integrated value (number of counts) of amounts of light having wavelengths of 380 to 750 nm is regarded as an integrated light amount of white color light (W). Furthermore, the light inputted to the integrating sphere 40 was measured by a CS-1000 spectral radiance meter (manufactured by Konica Minolta Sensing, Inc.), and integrate values of amounts of light in respective wavelength bands of blue color light (B), green color light (G) and red color light (R) were calculated as integrated light amounts of respective colors.

In the present specification, white color light (W) refers to light having wavelengths of 380 to 750 nm, blue color light (B) refers to light having wavelengths of 380 to 470 nm, green color light (G) refers to light having wavelengths of 470 to 580 nm, and red color light (R) refers to light having wavelengths of 580 to 750 nm.

Figure 5:
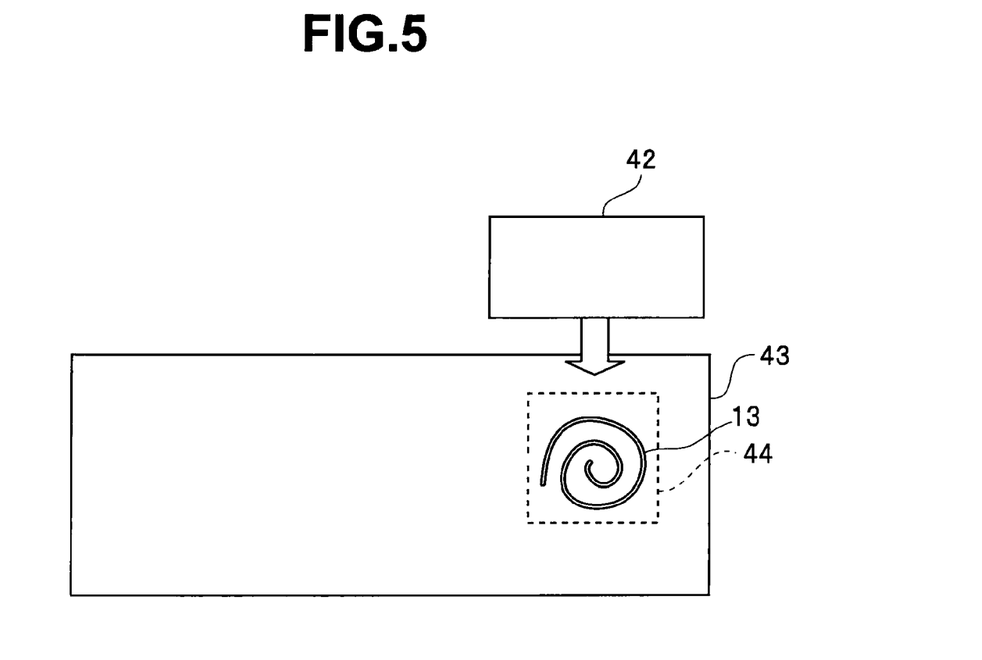
FIG. 5 is a diagram illustrating an X-ray resistance test method for the light guide for the endoscope according to the first embodiment.

Next, as illustrated in FIG. 5, the LG 13 was wound in whorl and placed in an X-ray irradiation area 44 of an irradiation stand 43. Then, using a radiography apparatus 42 (with a tube voltage of 100 kV, a tube current of 2.0 mA and wavelengths of 0.05 to 0.3 nm), the LG 13 was irradiated with an X-ray with a space of 30 cm between the LG 13 and the X-ray source until the irradiation amount reaches 2.5 Gy (gray).

In the X-ray resistance test, recovery processing was performed after the X-ray irradiation. In other words, recovery processing in which the LG 13 after the X-ray irradiation is connected again to the light source apparatus 24 to guide illuminating light of 64 lumen/mm$^2$ for 600 minutes was performed. This recovery processing is processing performed to evaluate an X-ray resistance closer to actual usage environments of endoscopes.

In other words, the recovery processing is one considering that where the endoscope 1 is used under X-ray irradiation, the light guide 13 is colored by the X-ray irradiation and is also made to recover from the colored state by the energy of light supplied from the light source. The present evaluation method is an accelerated test in which for example, the amount of X-ray irradiation is 2.5 Gy, that is, an amount of X-ray corresponding to an amount of X-ray several hundred times an amount of irradiation for, e.g., a normal surgery is applied at a time. Thus, the glass is firmly colored, and the effect of the recovery processing differs depending on the composition of the glass. However, it has otherwise been confirmed that such method is an appropriate method for a method for an accelerated test for X-ray resistance.

Then, the integrated light amount of white color light was measured before the X-ray irradiation and after the recovery processing, respectively, and a percentage of the integrated light amount after the recovery processing relative to the integrated light amount before the X-ray irradiation is determined as "white color light X-ray resistance value XR" and used as a measure of X-ray resistance. Here, the X-ray resistance value (XR) is rounded off to unit. Thus, where the X-ray resistance value (XR) is no less than 99.5%, the X-ray resistance value (XR) becomes 100%.

The white color light X-ray resistance value XR is an index indicating an amount of decrease in integrated light amount of white color light having wavelengths of 380 to 750 nm due to X-ray irradiation, and a white color light X-ray resistance value XR of 100% indicates full recovery to a state before X-ray irradiation from a colored state due to the X-ray irradiation, and a white color light X-ray resistance value XR of 70% indicates a 30% decrease in light amount, and thus, darkening.

The light amount is proportional to a transmittance of the LG 13, and thus, change in light amount of the LG 13 due to coloring can be regarded as change in transmittance. For example, a change in light amount by 10% corresponds to a change in transmittance by 10%.

Furthermore, since color rendition is important in in-vivo observation using an endoscope, change in light amount was also measured for each of green color light and blue color light in addition to white color light. Change in integrated light amount of blue color light (with wavelengths of 380 to 470 nm) was evaluated relative to an integrated light amount of green color light (with wavelengths of 470 to 580 nm), which indicates brightness, that is, in terms of (blue color light (B)/green color light (G)), and an X-ray resistance value XRR was calculated.

Next, a measurement method for the endoscope 1 with the LG 13 mounted therein will be described. This is a simulated mounting test in which an LG manufactured using a same manufacturing method as that for the LG used in the LG single body measurement has been mounted in the endoscope 1. For the endoscope 1, an endoscope for large intestine (having a length of 3.6 m and a distal end outer diameter of 15 mm) and an endoscope for small intestine (having a length of 3.6 m and a distal end outer diameter of 10 mm) were used.

Figure 6:
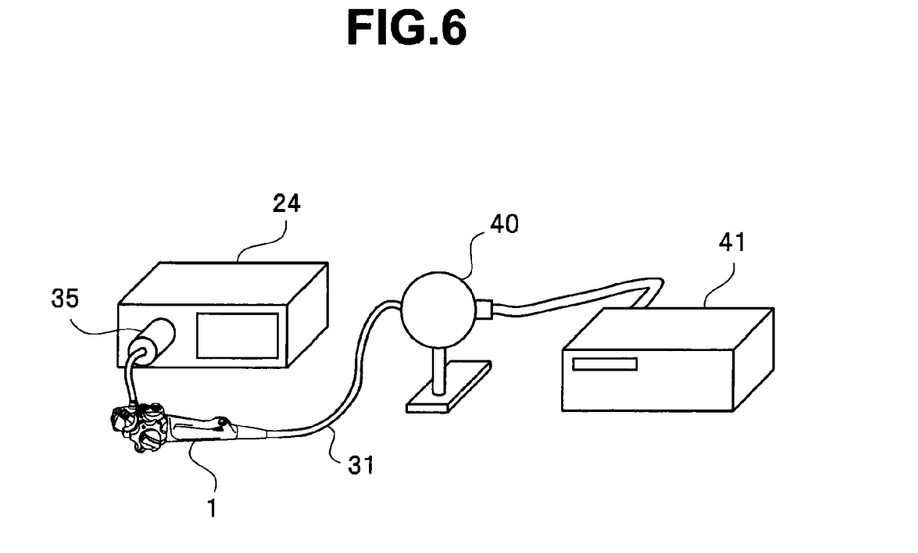
FIG. 6 is a diagram illustrating a light amount measurement method for the endoscope according to the first embodiment.
Figure 7:
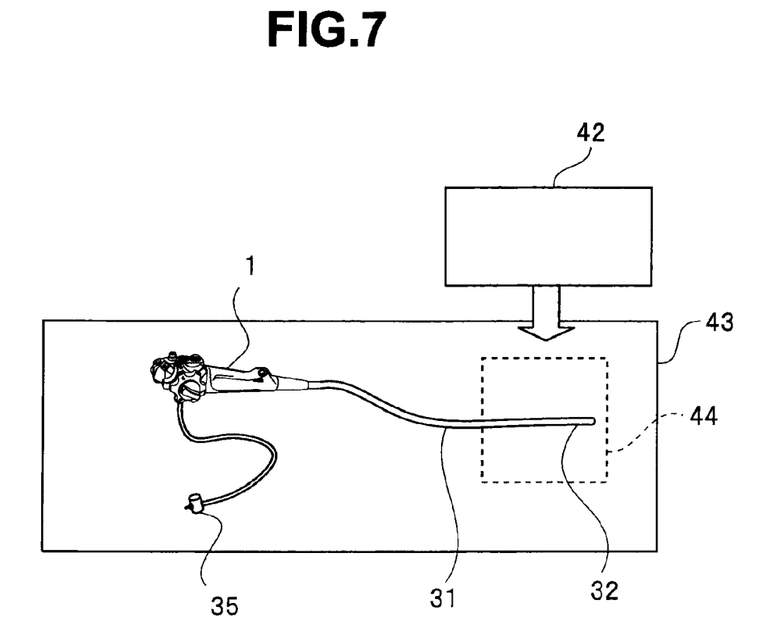
FIG. 7 is a diagram illustrating an X-ray resistance test method for the endoscope according to the first embodiment.

As illustrated in FIG. 6, the light amount measurement was performed using a system that is the same as one in FIG. 4. In other words, a light guide connector 35 of an endoscope 1 with an LG mounted therein in simulation is connected to a light source apparatus 24, and a light amount of light having a spectrum of 380 to 750 nm emitted from a distal end portion 32 was measured. Then, an amount of light of each of W, B and G colors was measured. Next, as illustrated in FIG. 7, an area of one meter from the distal end portion 32 of the endoscope 1 was irradiated with an X-ray. The amount of the X-ray irradiation was 2.5 Gy for the endoscope for large intestine and 14 Gy for the endoscope for small intestine. Subsequently, recovery processing that is the same as that in the test for the LG single body was performed and then a light amount measurement was performed again.

Furthermore, in the simulated mounting test, white color light imaging and NBI were actually performed, and brightness/color rendition of each endoscopic image was evaluated in four levels, "excellent", "good", "acceptable" and "not acceptable", based on the measurer's subjectivity.

First to Third Embodiments and Comparative Examples 1 and 2

Table 1 indicates results of an X-ray resistance test conducted for endoscopes 1, 1A and 1B according to first to third embodiments in which light guides 13 to 13B include fibers made of glasses having first to third compositions not including lead, an endoscope 1X according to comparative example 1 in which a light guide 13X includes fibers made of a lead-contained glass having a fourth composition, and an endoscope 1Y according to comparative example 2 in which a light guide 13Y includes fibers made of a lead-free glass having a conventional fifth composition. Configurations of the respective LGs used in the embodiments and the comparative examples in this study are described below.

1.7 wt % $La_2O_3$, 4.5 wt % $Al_2O_3$, 5.2 wt % MgO, 4.7 wt % $Na_2O$, 2.47 wt % $K_2O$ and 0.03 wt % $Sb_2O_3$, and a clad glass containing 67.1 wt % $SiO_2$, 10.1 wt % $B_2O_3$, 3.2 wt % $Al_2O_3$, 5.2 wt % ZnO, 2.4 wt % BaO, 7.2 wt % $Na_2O$ and 4.8 wt % $K_2O$.

Here, the refractive indexes of the core glasses of the light guides 13 to 13B are relatively high, ranging from 1.56 to 1.74, and thus, the light guides each have a high numerical aperture (NA) ranging from 0.46 to 0.90.

A numerical aperture (NA) falling within or exceeding the aforementioned range enables irradiation of an irradiation area according to the specifications of the medical endoscope, and a numerical aperture (NA) falling within or below the aforementioned range enables the optical system to be designed easily and manufactured at low cost.

In other words, the LG 13 for a medical endoscope needs to widely illuminate an inside of a body, and thus, requires a large numerical aperture NA of, for example, no less than

TABLE 1

| Item | | Endoscope 1 | Endoscope 1A | Endoscope 1B | Endoscope 1C | Endoscope 1D | Endoscope 1E | Endoscope 1X | Endoscope 1Y |
|---|---|---|---|---|---|---|---|---|---|
| X-ray resistance improvement means | | Improved LG | Improved LG | Improved LG | X-ray blocking LG (blades) | X-ray blocking LG (W rubber) | X-ray blocking LG (particles and coating) | Conventional Pb glass LG | Conventional Pb-free glass LG |
| White color light XR | | 68% | 91% | 100% | 90% | 92% | 80% | 90% | 33% |
| XRR | | 60% | 80% | 99% | 80% | 81% | 71% | 90% | 40% |
| Simulated endoscope for large intestine | White color light | Acceptable | Good | Excellent | Good | Good | Acceptable | Good | Not acceptable |
| | NBI | Acceptable | Good | Excellent | Good | Good | Acceptable | Excellent | Not acceptable |
| Simulated endoscope for small intestine | White color light | Acceptable | Good | Excellent | Good | Good | Acceptable | Good | Not acceptable |
| | NBI | Acceptable | Good | Excellent | Good | Good | Acceptable | Excellent | Not acceptable |

The LG 13 in the endoscope 1 is made of a core glass containing 34.0 wt % $SiO_2$, 7.0 wt % $B_2O_3$, 27.0 wt % BaO, 15.0 wt % $La_2O_3$, 9.0 wt % ZnO, 3.7 wt % $Na_2O$, 0.3 wt % $Na_2SO_4$ and 0.03 wt % $Sb_2O_3$, and a clad glass containing 75.14 wt % $SiO_2$, 10.07 wt % $B_2O_3$, 1.06 wt % $Al_2O_3$, 2.57 wt % CaO and 11.16 wt % $Na_2O$.

The LG 13A in the endoscope 1A is made of a core glass containing 40.03 wt % $SiO_2$, 0 wt % $B_2O_3$, 26.87 wt % BaO, 9.27 wt % $La_2O_3$, 3.00 wt % $Ta_2O_5$, 12.08 wt % ZnO, 6.02 wt % $Na_2O$, 2.18 wt % $K_2O$, 0.32 wt % $Na_2SO_4$ and 0.005 wt % $Sb_2O_3$, and having an Fe content of 0.40 ppm, a Cr content of 0.01 ppm, a Co content of 0.01 ppm, an Ni content of 0.01 ppm and a Pt content of 0.20 ppm, and a clad glass containing 75.14 wt % $SiO_2$, 10.07 wt % $B_2O_3$, 1.06 wt % $Al_2O_3$, 2.57 wt % CaO and 11.16 wt % $Na_2O$.

The LG 13B in the endoscope 1B is made of a core glass containing 36.40 wt % $SiO_2$, 1.90 wt % $B_2O_3$, 26.87 wt % BaO, 8.70 wt % $La_2O_3$, 4.99 wt % $Ta_2O_5$, 6.03 wt % ZnO, 7.42 wt % $Na_2O$, 2.18 wt % $K_2O$, 0.50 wt % $Na_2SO_4$, 0.001 wt % $Sb_2O_3$, and having an Fe content of 0.40 ppm, a Cr content of 0.01 ppm, a Co content of 0.01 ppm, an Ni content of 0.01 ppm and a Pt content of 0.00 ppm, and a clad glass containing 75.14 wt % $SiO_2$, 10.07 wt % $B_2O_3$, 1.06 wt % $Al_2O_3$, 2.57 wt % CaO and 11.16 wt % $Na_2O$.

The LG 13X in the endoscope 1X is made of a Pb-contained core glass containing 72.2 wt % $SiO_2$, 20.0 wt % PbO, 0.7 wt % $Al_2O_3$, 1.2 wt % CaO, 2.3 wt % $Na_2O$ and 3.6 wt % $K_2O$, and a clad glass containing 71.9 wt % $SiO_2$, 3.4 wt % $B_2O_3$, 0.7 wt % $Al_2O_3$, 5.2 wt % MgO, 3.7 wt % CaO and 14.5 wt % $Na_2O$.

The LG 13Y in the endoscope 1Y is made of a core glass containing 43.4 wt % $SiO_2$, 14.5 wt % $B_2O_3$, 23.5 wt % BaO, 0.55 compared to those of, e.g., communication optical fibers. LGs for general use have an NA ranging from 0.62 to 0.66, and high NA type ones have an NA of, e.g., 0.72 or 0.87.

Also, a refractive index nd of a core glass falling within or exceeding the aforementioned range enables obtainment of a required numerical aperture (NA), and a refractive index nd of a core glass falling within or below the aforementioned range enables the optical system to be designed easily and manufactured at low cost.

Meanwhile, clad glasses containing silica as a main component and also containing, e.g., alkalis and alkali earths have a refractive index nd ranging from 1.47 to 1.52.

The core glasses in the light guides 13 to 13 have a refractive index nd ranging from 1.56 to 1.74, and thus, meet the following requirements:

A composition containing (A) no more than 50 wt % ($SiO_2+B_2O_3$), (B) 20 to 45 wt % $SiO_2$, (C) 1 to 10 wt % $B_2O_3$, (D) 20 to 35 wt % (BaO+SrO), (D2) 0 to 15 wt % SrO, (E) 0 to 30 wt % ZnO, (F) 0.1 to 30 wt % one or more selected from $R_2O_3$ (R is La, Gd, Y or Lu) and $R_2O_5$ (R is Ta or Nb), (G) 0 to 10 wt % $Al_2O_3$, (H) 0 to 8 wt % $ZrO_2$, (I) 0 to 10 wt % alkali metal oxide and (J) 0 to 0.15 wt % $Sb_2O_3$; a Fe content of no more than 1.0 ppm, a Cr content of no more than 0.1 ppm, a Co content of no more than 0.01 ppm and an Ni content of no more than 0.1 ppm.

The core glasses in the light guides 13A and 13B further meet the following requirements:
(A) 20 to 55 wt % $SiO_2$, (B1) 0 to 4.0 wt % $B_2O_3$, (B2) neither $P_2O_5$ nor $GeO_2$ contained, (C) 25 to 72 wt % (BaO+SrO+$La_2O_3$+$Lu_2O_3$+$Ta_2O_5$+$Gd_2O_3$+$WO_3$), (D) 0 to 30 wt % ZnO, (E) no $Al_2O_3$ contained, (F) no $ZrO_2$ contained, (G) neither PbO nor $As_2O_3$ contained, (H) 0 to 15 wt % ($Na_2O+K_2O$), (I) 0 to 0.050 wt % $Sb_2O_3$ and (J) 0.26 to 1.63 wt % ($Na_2SO_4$+$K_2SO_4$).

Furthermore, the core glasses in the light guides 13A and 13B each have an Fe content of no more than 3 ppm, a Cr content of no more than 0.03 ppm, a Co content of no more than 0.01 ppm, an Ni content of no more than 0.02 ppm and a Pt content of no more than 0.2 ppm.

The core glass in the light guide 13B further meets the following requirements:
(B11) 0 to 2.0 wt % $B_2O_3$, (C1) 39 to 46 wt % ($BaO+SrO+La_2O_3+Lu_2O_3+Ta_2O_5+Gd_2O_3+WO_3$), (D1) 4 to 16 wt % ZnO, (H1) 4 to 10 wt % $Na_2O$ and/or $K_2O$, (I1) 0.001 to 0.010 wt % $Sb_2O_3$, (J1) 0.32 to 0.78 wt % $Na_2SO_4$ and/or $K_2SO_4$.

Use of a core glass having a composition disposed in, for example, examples 1 to 27, in particular, examples 22 to 27 in Japanese Patent Application Laid-Open Publication No. 2011-116621 also enables manufacture of an LG having characteristics similar to those of the light guide 1A if the core glass has impurity contents meeting the requirements described above.

The clad glasses were selected based on the points, such as refractive index, difference in thermal expansion coefficient from the core glass, wettabilities of core glass and clad glass and difficulty in mutual component diffusion.

As a result of making an association between the X-ray resistance values XR indicated in Table 1 and the user's feeling in actual endoscopic image observation, in the case of white color light, an XR of 68% is a permissible lower limit under which the user recognizes that the image was apparently darkened. Meanwhile, no substantial change was recognized where XR is no less than 89%, and no change was recognized where XR is 100%.

From, e.g., the results of the simulated mounting tests, in terms of color rendition, an X-ray resistance value XRR of 60% was a permissible lower limit enabling the user to make judgment of an image of a diseased part with good reproducibility because an intensity of blue color light including information on a tumor and/or blood vessels is reduced. Meanwhile, in the case of an XRR of no less than 80%, the user did almost not feel the coloring, and in the case of an XRR of no less than 90%, the user did not feel the coloring at all.

As indicated in Table 1, the endoscope 1Y according to comparative example 2 including fibers made of a lead-free glass having a conventional composition has a poor X-ray resistance. The endoscope 1X according to comparative example 1 including fibers made of a lead-contained glass has a good X-ray resistance but does not respond to environmental problems.

On the other hand, the endoscopes 1 to 1B according to the embodiments have a lead-free glass LG, but have an excellent X-ray resistance.

In other words, the fibers in the light guides in the endoscopes 1 to 1B have a white color light X-ray resistance value XR (ratio between an integrated light amount of light of 380 to 750 nm after an X-ray resistance test in which the recovery processing of guiding light of 64 lumen/mm² for 600 minutes is performed after 2.5 Gy X-ray irradiation and an integrated light amount before the X-ray resistance test) of no less than 67%, and an X-ray resistance value XRR (ratio between (a blue color light amount ratio indicated by an integrated light amount of light of 380 to 470 nm/an integrated light amount of light of 470 to 580 nm) and the blue color light amount ratio before the X-ray resistance test) of no less than 60%.

Furthermore, the endoscope 1A has a white color light X-ray resistance value XR of no less than 89% and an X-ray resistance value XRR of no less than 80%. Furthermore, the endoscope 1B has a white color light X-ray resistance value XR of 100% and an X-ray resistance value XRR of no less than 90%.

Furthermore, the numerical aperture (NA) of the LG13 is 0.46 to 0.90, which meets specifications for endoscopes. Furthermore, with the endoscope 1 to 1B according to embodiments, color rendition of color endoscopic images picked by the respective image pickup sections 33 does not deteriorate, enabling, e.g., proper examination.

Fourth Embodiment

Next, an endoscope 1C according to a fourth embodiment will be described. The endoscope 1C includes an LG 13 having glass compositions that are the same as those of the endoscope 1 and is similar to the endoscope 1, and thus, components that are the same as those of the endoscope 1 are provided with reference numerals that are the same as those of the endoscope 1 and description thereof will be omitted.

As already described, the endoscopes 1A and 1B have very good characteristics. However, compared to the endoscope 1, the manufacturing cost of the LGs is high. This is because the LGs used in the endoscopes 1A and 1B require extremely high level management of a dedicated furnace, raw materials and manufacturing processes in order to avoid impurity contamination while the endoscope 1 only requires a level of management that is the same as that required in normal optical glass manufacturing facilities and manufacturing processes. Thus, characteristic improvement was studied using the relatively-inexpensive LG in the endoscope 1.

Figure 8:
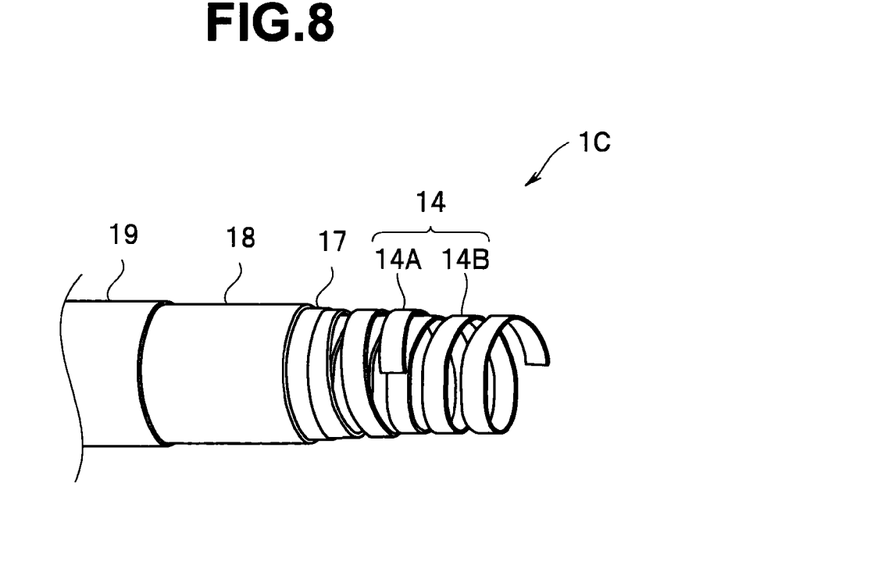
FIG. 8 is a diagram illustrating an X-ray blocking member for an endoscope according to a second embodiment.

As illustrated in FIG. 8, the endoscope 1C according to the present embodiment includes a flex 14, which is a flexible X-ray blocking member that blocks X-rays. Here, an insertion portion 31 of the endoscope 1C includes a coating layer 19, a resin layer 18, a mesh 17, and the flex 14 (an outer flex 14A and an inner flex 14B) in this order from the outside, and an inside of the insertion portion 31 is a hollow to which, e.g., the LG 13 is inserted.

As already described, it is known that an X-ray blocking member is used in a communication optical fiber used under a strong radiation exposure environment. However, for endoscopes, it has been difficult to use known blocking members for communication optical fibers from the viewpoints of, e.g., reduction in diameter of the insertion portion 31, living body safety, color rendition of color images and flexibility maintenance.

Here, an outer diameter of an insertion portion 31 of endoscopes will be described. In many endoscopes for large intestine, the outer diameter is 10 to 13 mm, and around 15 mm at the maximum. In endoscopes for small intestine, the outer diameter is 9 to 10 mm, in endoscopes for ureter, the outer diameter is 2.8 to 3.5 mm, and in endoscopes for biliary tract, the outer diameter is around 5 mm. As the outer diameter of the endoscope is larger, the burden of the patient increases. Thus, X-ray blocking means such as, for example, covering an outer circumferential portion of an LG 13 with, e.g., a thick SUS, cannot be used because the outer diameter cannot be maintained.

As a result of diligent consideration, the inventors studied means for providing an X-ray resistance that guarantees observation and/or examination, suppressing an outer diameter increase to no more than 0.4 mm for reduction in patients' burden and providing an industrially practical price for, for example, a medical endoscope of a diameter of 15 mm.

The LG 13 in the endoscope 1C is a lead-free glass LG having compositions that are the same as those of the endoscope 1. However, in the endoscope 1C, a tungsten ribbon having a thickness of 0.1 mm is used as the outer flex 14A of the insertion portion 31. While the insertion portion 31 has a total length of 3.6 m, the tungsten ribbon is wound as the outer flex 14A on an area of 3 m and 45 cm on the proximal end portion side of the insertion portion 31 except the area of 15 cm from a distal end portion 32 to a bending portion thereof. Furthermore, a material for the inner flex 14B having a thickness of 0.1 mm has been changed to SUS310L having the same thickness and containing a larger amount of component having a higher X-ray blocking ability such as Ni or Mo compared to SUS304.

As indicated in Table 1, the endoscope 1C has a largely-improved X-ray resistance compared to the endoscope 1Y (comparative example 2) using SUS304 for the outer flex 14A and the inner flex 14B.

Figure 9:
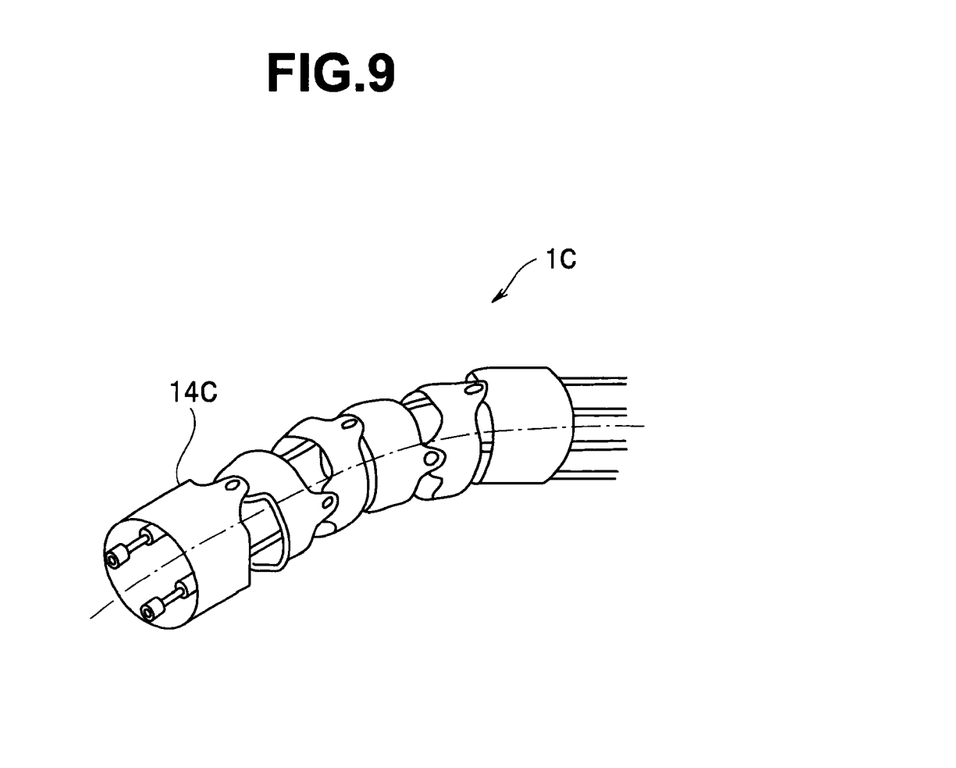
FIG. 9 is a diagram illustrating an X-ray blocking member according to the endoscope of the second embodiment.

A mode of the X-ray blocking member is not limited to the flex 14, and e.g., a net-like tube (mesh 17) in the insertion portion 31 illustrated in FIG. 8 or a flexible tube (blades 14C) in the insertion portion 31 illustrated in FIG. 9 may be employed.

In other words, as a result of combination of an LG 13 made of a glass having an X-ray resistance of no less than a predetermined value and an X-ray blocking material enables provision of a more excellent X-ray resistant characteristic while the outer diameter of the endoscope is suppressed to the minimum.

Furthermore, even though a desired X-ray resistant characteristic cannot be obtained merely by changing, e.g., the glass composition, combination of provision of an X-ray blocking member with such change enables obtainment of an endoscope having a desired X-ray resistant characteristic.

The X-ray blocking material is made of a material containing a metal, an oxide, a nitride, a compound, a mixture or an alloy as a main component, the metal, the oxide, the nitride, the compound, the mixture or the alloy containing at least one metal element selected from V, Cr, Mn, Fe, Co, Ni, Cu, Zn, Ga, Zr, Sr, Y, Nb, Mo, Tc, Ru, Rh, Pd, Ag, In, Ba, Hf, Ta, W, Re, Os, Ir, Pt, Au, Bi, lanthanoid and actinoid. In general, as the density of the substance is higher, the X-ray blocking ability is higher. Accordingly, while metals in the VIII to IX groups in the periodic table have maximum X-ray blocking effects, metals in the IVA to VB groups exhibit high X-ray blocking, and fifth and sixth-period elements have especially high X-ray blocking effects.

For example, in the fourth period, Ni has a highest X-ray blocking ability, and next to that, Cu, Co and Fe have relatively high blocking abilities. In the fifth period, the metals generally have higher X-ray blocking abilities compared to those in the fourth period, and, e.g., Ru, Rh and Pd each have a relatively high blocking ability. In the sixth period, the metals generally have higher X-ray blocking abilities compared to those in the fifth period, and W, Re, Os, Ir, Pt and Au each have a relatively high blocking ability.

Here, in actual use, it is necessary to install an X-ray blocking member without impairing the fundamental features of the endoscope. Furthermore, it is necessary to select a proper material comprehensively in views of e.g., chemical stability, workability and cost. Furthermore, it is necessary to select a safe material for living bodies as an X-ray blocking member assuming that the material may come into contact with a living body owing to, e.g., breakage of the endoscope.

From these perspectives, toxicants such as Tl and radioactive substances such as Th are deleted from the objects to be selected as an X-ray blocking member. Furthermore, in terms of cost, Pt, Au and Ir or the like are expensive and thus, a range of use thereof is industrially limited. Ag, Ba, Sr or the like have low X-ray blocking abilities compared to W, Ta and Bi, and thus, a range of use thereof is limited; however, such elements are relatively inexpensive. In the case of Ba, Sr or the like, there are cases where a compound such as a sulfate can also be used.

In particular, a metal, a metal oxide or an alloy of W, Ta or Bi has a high X-ray blocking ability and has a balance between safety and cost, and thus, particularly preferable as an X-ray blocking member material for an endoscope.

Metals, metal compounds and alloys are hard in a bulk state, requiring provision of flexibility. Thus, in order to use the metals, the metal compounds and the alloys as an X-ray blocking member, a material having rubber-like elasticity such as a thermoset elastomer or a thermoplastic elastomer is made to contain any of the aforementioned metal/metal components, a metal is formed into a ribbon shape or a mesh, or the metals, the metal compounds and the alloys in a form of a thin layer or particles are added to the LG 13.

As already described, in the case of, for example, a ribbon made of a tungsten metal, a thickness of 0.05 to 0.2 mm is preferable. Within that range, desired X-ray blocking can be provided while the flexibility is ensured.

An SUS containing, e.g., Fe, Cr, Ni or Mo also has an X-ray blocking effect, but the effect is not high. However, as already described, an SUS is used as a material for a flex in order to maintain adequate bendability of the endoscope. Although a commonly-used flex is made of SUS304, use of, e.g., austenite-based SUS310, SUS836 or SUS890 having a higher X-ray blocking ability than that of SUS304 enables obtainment of a further higher X-ray blocking effect.

Furthermore, a high-density material containing any of the elements in the fifth and sixth periods, which have high X-ray blocking abilities as described above, for example, a material containing W, Ta or Bi at high density generally has high rigidity. In order to maintain adequate bendability of the endoscope, it is effective to combine two members, i.e., an X-ray blocking member made of a high-density material and an SUS member and use the combination as a flex 14.

As described above, for an X-ray blocking member for medical endoscopes, not only selection of materials but also a balance among X-ray blocking ability, low invasiveness and cost according to a part in which X-ray is blocked is important. Furthermore, in medical endoscopes, an X-ray blocking member has a large effect for, e.g., prevention of deterioration of color rendition, which has not been a problem in known optical fibers, and thus, it was necessary to make efforts that are completely different from those for known communication optical fibers used under strong radiation exposure environments.

Fifth Embodiment

Next, an endoscope 1D according to a fifth embodiment will be described. The endoscope 1D includes an LG 13 having glass compositions that are the same as those of the endoscope 1 and similar to the endoscope 1, and thus, components that are the same as those of the endoscope 1 are provided with reference numerals that are the same as those of the endoscope 1, and description thereof will be omitted.

Figure 10:
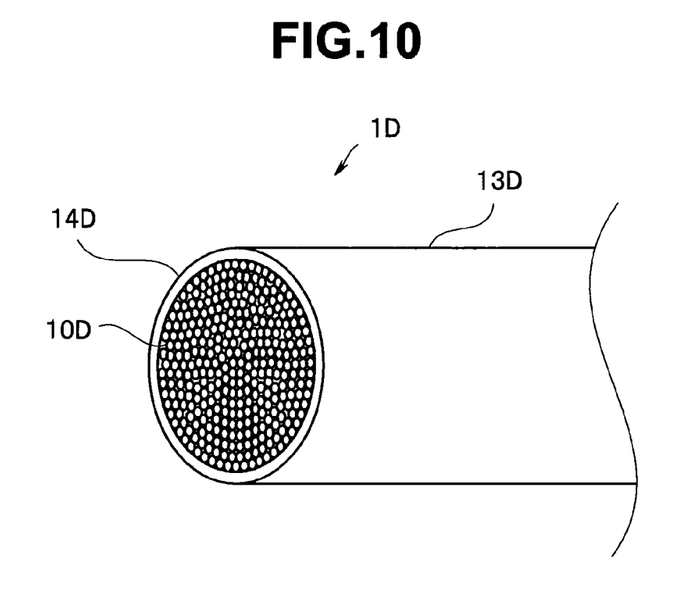
FIG. 10 is a diagram illustrating a light guide for an endoscope according to a third embodiment.

As illustrated in FIG. 10, in the endoscope 1D, a resin sheet 14D, which is a commercially-available tungsten rubber sheet having a specific gravity of 11.6 and a thickness of 0.2 mm was wound as an X-ray blocking member on an insertion portion 31. The resin sheet 14D was provided not in an area of 15 cm from a distal end to a bending portion, but in an area of approximately 3 m and 85 cm on the proximal end portion side.

As indicated in Table 1, the endoscope 1D has a substantially-improved X-ray resistance compared to the endoscope 1Y (comparative example 2) including no X-ray blocking material. Also, substantially-similar results were obtained using a W-mixed ethylene vinyl rubber sheet (with a specific gravity of 13.4) having a thickness of 0.1 mm in place of the resin sheet 14D.

Also, e.g., an LG covering tube such as a silicone tube or a Gore-Tex (registered trademark) tube, a covering rubber for a bending portion, a rubber for endoscopes, such as a resin, which is used for a flexible portion or a resin member may be used as an X-ray blocking member.

Even though a material having high bending resistance such as a rubber is used as an X-ray blocking member having flexibility, the material may be broken if the material is used in a bending portion that is largely and sharply bent. However, disposition of such material only in a flexible portion that is gently bent enables provision of both adequate bendability and imaging performance (X-ray resistance).

An area of an endoscope in which an X-ray blocking material is disposed may be limited to a portion irradiated with an X-ray. In other words, the portion of the endoscope subjected to X-ray irradiation is mainly the insertion portion 31. The insertion portion 31 is a portion in which the LG 13 is included, and disposition of a blocking effect member in the insertion portion 31 enables reduction in X-ray exposure of the LG 13 inserted through an inside of the insertion portion 31.

In other words, although in the X-ray resistance evaluation test for an LG, the total length of the LG is irradiated with an X-ray, in an actual endoscope, only an area of a predetermined length from a distal end of the insertion portion 31 is irradiated with an X-ray. For example, in an endoscope for large intestine, an X-ray irradiation area has a length of around 1 m including a bending portion of 15 cm. Thus, even though no X-ray blocking member is provided in the bending portion, the operability can be maintained to be the same as that of the conventional ones by providing an X-ray blocking member in the remaining portion with a length of approximately 85 cm.

The X-ray irradiation area differs depending on the endoscope. For example, in an endoscope, an area irradiated with an X-ray is an area of 40 cm from a distal end. As a result of an X-ray resistance test having been conducted for each of three types of areas covered by an X-ray blocking member, 24 cm, 28 cm and 32 cm in the endoscope, the blocking area of 28 cm was an acceptable lower limit. In other words, an X-ray blocking member is acceptable if the X-ray blocking member has an area of no less than 70% relative to the area irradiated with an X-ray. From the result, it is only necessary that the X-ray blocking member covers a length of the insertion portion 31 that is no less than 70%, preferably no less than 85%, relative to a length of the insertion portion 31 irradiated with an X-ray.

Sixth Embodiment

Next, an endoscope 1E according to a sixth embodiment will be described. The endoscope 1E includes an LG 13 having glass compositions that are the same as those of the endoscope 1 and is similar to the endoscope 1, components that are the same as those of the endoscope 1 are provided with reference numerals that are the same as those of the endoscope 1, and description thereof will be omitted.

Figure 11:
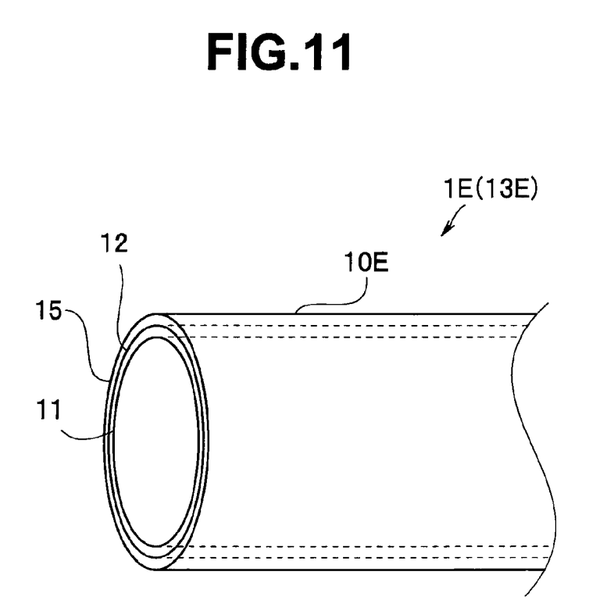
FIG. 11 is a diagram illustrating a light guide fiber for an endoscope according to a fourth embodiment.
Figure 12:
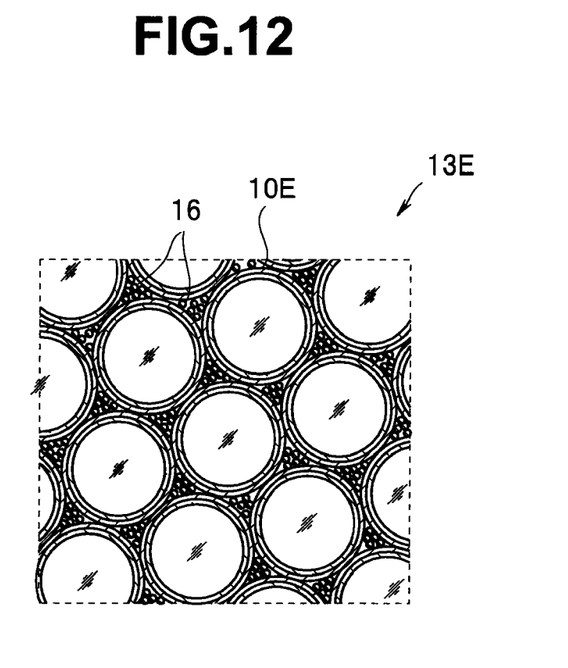
FIG. 12 is a cross-sectional diagram illustrating a light guide for an endoscope according to a fifth embodiment.

As illustrated in FIG. 11, 2800 fibers 10E in a light guide 13E having a bundle diameter of 1.95 mm in the endoscope 1E each include an X-ray blocking coating layer 15. Furthermore, as illustrated in FIG. 12, the light guide 13E includes numerous X-ray blocking particles 16 in gaps among the fibers 10E having an outer diameter of 30.5 µm.

The X-ray blocking coating layer 15, which is formed using tungsten oxide ($WO_3$) by means of an atmospheric-pressure plasma method, has a thickness of 1 µm. The X-ray blocking particles 16, which are made of metal tungsten, have a diameter of 0.01 to 1 µm.

A method for manufacturing the light guide 13E will be described below. First, opposite ends of each of 2800 fibers 10E having a length of 1 m, on an outer circumferential portion of which a tungsten oxide film of 1 µm have uniformly been formed, are temporarily fixed. The X-ray blocking particles 16 are poured over the temporarily-fixed light guide, and the light guide is largely and vertically shaken with the opposite ends maintained horizontally. As a result of distribution processing and shaking processing of the X-ray blocking particles 16 are repeated 30 times, the X-ray blocking particles 16 are uniformly dispersed in the light guide. The light guide is inserted into a silicone tube, and opposite ends of thereof are fixed by a stainless tube (having an inner diameter of 1.95 mm and an outer diameter of 2.6 mm) using an adhesive. An occupancy P of the particles in the silicone tube in the light guide 13E was 0.75%.

Here, the particle occupancy P is an occupancy in a cross-section of the light guide 13E, which was calculated by means of microscopic imaging after the light guide 13E being immersed in an epoxy resin to fix the particles and then the cross-section being subjected to grinding.

Occupancy(%)=Total area of particles contained in LG cross-section/cross-section of LG bundle)×100

As indicated in Table 1, as a result of the X-ray resistance test, the endoscope 1E has a white color light XR of 80%, which is a 17% increase compared to the white color light XR (68%) of the endoscope 1 including no X-ray blocking member.

For materials for the X-ray blocking coating layer 15 and the X-ray blocking particles 16, various types of materials described in the fifth embodiment can be used. In the case of $WO_3$, if the X-ray blocking coating layer 15 has a thickness of no less than 0.5 µm, the light amount in the endoscope 1 increases by no less than 10%, that is, even if at least the X-ray blocking coating layer 15 has a thickness of no less than 0.5 µm, the effect of providing a light amount of no less than 110% can be provided, and if the X-ray blocking coating layer 15 has a thickness of no more than 3 µm, it is possible to prevent the light guide from losing the flexibility or the fibers from being broken during processing.

Furthermore, in the case of $WO_3$, the X-ray blocking particles 16 are effective if the occupancy P of the X-ray blocking particles 16 is no less than 0.5%. As the occupancy P is higher, the X-ray resistance value XR increases, and if the occupancy P is no more than 5%, the light guide is not broken when the light guide is bent.

For a method for forming the X-ray blocking coating layer 15, i.e., electroplating, non-electrolytic plating, organic metal liquid application or organic metal paste application may be used.

As described above, the endoscope 1E including the light guide 13E in which the fibers 10E each having the X-ray blocking coating layer 15 and the X-ray blocking particles 16 are provided in the gaps among the fibers 10E has a further improved X-ray resistance.

Also, although the endoscopes 1A and 1B exhibit more favorable X-ray resistant characteristics than that of the endoscope 1, by means of selection of glass compositions for the light guide 13, the endoscopes 1A and 1B can have higher performance by use of various configurations described for the endoscopes 1C to 1E.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
an insertion portion including an image pickup section and an illumination section in a distal end portion thereof; and
a light guide inserted through an inside of the insertion portion, the light guide including a plurality of fibers made of a glass not containing lead, the plurality of fibers guiding illuminating light from a light source apparatus connected to a proximal end portion side to the illumination section, the light guide having a numerical aperture (NA) of 0.46 to 0.90,
wherein a core glass of the fibers has a refractive index nd of 1.56 to 1.74, and has a composition of (A) 20 to 55 wt % $SiO_2$, (B1) exceeding 2.0 wt % to equal to or less than 4.0 wt % $B_2O_3$, (B2) neither $P_2O_5$ nor $GeO_2$ contained, (C) 25 to 72 wt % ($BaO+SrO+La_2O_3+Lu_2O_3+Ta_2O_5+Gd_2O_3+WO_3$), (D) 0 to 30 wt % ZnO, (E) no $Al_2O_3$ contained, (F) no $ZrO_2$ contained, (G) neither PbO nor $As_2O_3$ contained, (H) 0 to 15 wt % ($Na_2O+K_2O$), (I) 0 to 0.050 wt % $Sb_2O_3$ and (J) 0.26 to 1.63 wt % ($Na_2SO_4+K_2SO_4$).

2. The endoscope according to claim 1, wherein an integrated light amount of light of 380 to 750 nm after an X-ray resistance test in which recovery processing of guiding light of 64 lumen/mm² for 600 minutes is performed after irradiation with an X-ray of 2.5 Gy is no less than 67% of an integrated light amount before the X-ray resistance test, and a blue color light amount ratio, indicated by a ratio of integrated light amount of light of 380 to 470 nm to integrated light amount of light of 470 to 580 nm, after the X-ray resistance test is no less than 60% of a blue color light amount ratio before the X-ray resistance test.

3. The endoscope according to claim 2, wherein at least one of an inner portion and an outer portion of the light guide includes a flexible X-ray blocking member that blocks an X-ray.

4. The endoscope according to claim 3, wherein the X-ray blocking member covers a length of the insertion portion, the length being no less than 70% relative to a length of the insertion portion subjected to X-ray irradiation.

5. The endoscope according to claim 3, wherein the X-ray blocking member is made of a metal, a metal oxide or an alloy of W, Ta or Bi.

6. The endoscope according to claim 2, wherein each of the plurality of fibers includes an X-ray blocking coating layer that blocks an X-ray at a surface thereof.

7. The endoscope according to claim 6, wherein the X-ray blocking coating layer is made of a metal, a metal oxide or an alloy of W, Ta or Bi.

8. The endoscope according to claim 7, wherein the X-ray blocking coating layer has a thickness of no less than 0.5 μm and no more than 3 μm.

9. The endoscope according to claim 2, wherein the integrated light amount of light of 380 to 750 nm in the light guide after the X-ray resistance test is no less than 110% of an integrated light amount in a light guide in an endoscope not including the X-ray blocking member after the X-ray resistance test.

10. The endoscope according to claim 2, wherein X-ray blocking particles that block an X-ray are provided in a gap between the plurality of fibers.

11. The endoscope according to claim 10, wherein the X-ray blocking particles are made of a metal, a metal oxide or an alloy of W, Ta or Bi.

12. The endoscope according to claim 11, wherein an occupancy of the X-ray blocking particles in a tube housing the plurality of fibers is no less than 0.5% and no more than 5%.

13. The endoscope according to claim 1, wherein the image pickup section picks up a color image.

14. The endoscope according to claim 1, wherein the core glass of the fiber has a composition of (C1) 39 to 46 wt % ($BaO+SrO+La_2O_3+Lu_2O_3+Ta_2O_5+Gd_2O_3+WO_3$), (D1) 4 to 16 wt % ZnO, (H1) 4 to 10 wt % ($Na_2O+K_2O$), (I1) 0.001 to 0.010 wt % $Sb_2O_3$ and (J1) 0.32 to 0.78 wt % ($Na_2SO_4+K_2SO_4$).

* * * * *